July 24, 1956 H. E. HIRAOKA Plant Pat. 1,499
PEACH TREE
Filed Aug. 12, 1955
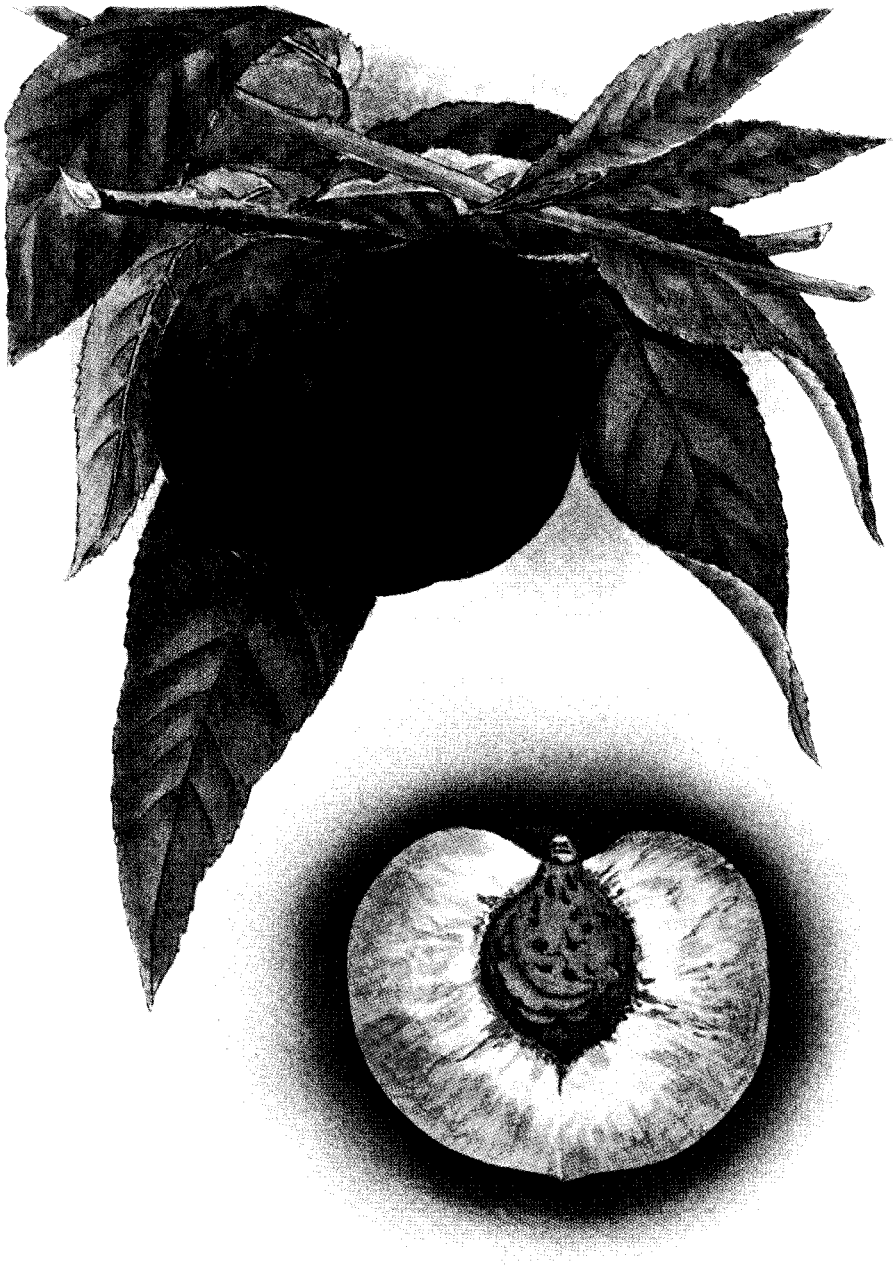
WITNESS
Addison E. Avery
INVENTOR
Harry E. Hiraoka United States Patent Office Plant Pat. 1,499
Patented July 24, 1956

1,499

PEACH TREE

Harry E. Hiraoka, Fowler, Calif.

Application August 12, 1955, Serial No. 528,145

1 Claim. (Cl. 47—62)

This discovery relates to a new and distinct variety of peach tree which bears large, rather uniform, yellow with slight streaks of red, firm fleshed, full freestone fruit having a deep glossy red skin.

The present variety of peach tree is distinctively characterized, in comparison to other varieties, by fruit which is larger, more uniform in size and having a deeper red color than the Gold Dust peach (United States Plant Patent No. 1,144); by a ripening period of about the same period as the Merrill Gem peach (United States Plant Patent No. 868) and about thirty days earlier than the July Elberta peach (United States Plant Patent No. 15); by a stone that is completely free as compared to the Merrill Gem peach (United States Plant Patent No. 868).

Further, the fruit of the present variety of peach is advantageously characterized, for maket use, local or long distance, by its superlative shipping and carrying qualities; ripening uniformly and evenly; good to best eating quality because of relative non-acid taste; fiesh having few fibers; excellent flavor which is fine and melting; and no split pits.

This new and distinct variety of peach tree was discovered by me in an orchard on my peach ranch near Fowler, Fresno County, State of California, growing as a bud mutation on a July Elberta peach tree. When such bud mutation came into bearing I immediately recognized its novel features, as described above.

Having found that the variety bore fruit which had substantial commercial potential due to its size, color and full freestone characteristics, as well as its flavor, I determined to undertake propagation of the variety. This was accomplished by me on my peach ranch, located as aforesaid, by budding the variety on a Lovell peach (unpatented) seedling. When such asexual reproduction grew to maturity and came into bearing it was found to carry forward all of the characteristics of the parent. Subsequent asexual reproduction of the variety likewise have run true.

In the drawing there is illustrated one of the fruit, together with twigs and leaves and a cross section of one of the fruit with the stone exposed and in place.

Referring now more to the pomological details of this new and distinct variety of peach tree, the following is an outline description thereof; all major color plate identifications being by reference to Maerz and Paul Dictionary of Color.

Tree:
- *Size.*—Large.
- *Vigor.*—Vigorous.
- *Growth.*—Upright.
- *Density.*—Dense.
- *Form.*—Vase formed.
- *Hardiness.*—Hardy.
- *Production.*—Very productive.
- *Bearing.*—Regular bearer.

Trunk:
- *Size.*—Medium stocky.
- *Surface.*—Smooth.

Branches:
- *Size.*—Medium.
- *Surface.*—Smooth.
- *Color.*—Brown, green tinged.
- *Lenticels.*—Numerous and inconspicuous.

Leaves:
- *Size.*—Medium. Average length—4–5". Average width—1–1½".
- *Form.*—Lanceolate, pointed.
- *Thickness.*—Medium.
- *Surface.*—Smooth.
- *Color.*—Top side—medium to dark green (22–L–6 shading to 23–L–7). Under side—lighter green (21–K–6). Heavy mid rib underside—light green (19–K–2).
- *Margin.*—Crenate.
- *Petiole.*—Medium length; medium thickness.
- *Glands.* — Average number — two. Opposite; reniform; medium size; green. Position—mostly on petiole.
- *Stipules.*—None.

Flower Buds:
- *Hardiness.*—Hardy.
- *Size.*—Medium in length; medium in size.
- *Form.*—Plump; free; pubescent.

Flowers:
- *Size.*—Medium.
- *Color.*—Salmon.
- *Date of first bloom.*—March 9.
- *Date of full bloom.*—March 14.

Fruit:
- *Maturity when described.*—Eating ripe.
- *Date of first picking.*—June 12, 1955.
- *Date of last picking.*—June 17, 1955.
- *Size.*—Large for season of ripening. Average diameter axially—3¼" to 3¾". Average transversely in suture plane—3" to 3½".
- *Form.*—Uniform; oblate; slightly compressed transversely.
- *Suture.*—Distinct. Moderately deep and apparent for entire circumference, but faint on dorsal side.
- *Ventral surface.*—Moderately lipped both sides. Lips slightly unequal.
- *Cavity.*—Abrupt, circular, with suture showing on one side. Average depth—½". Average breadth —½".
- *Base.*—Rounded.
- *Apex.*—Short; depressed.
- *Pistil point.*—Oblique.

Skin:
- *Texture.*—Medium thickness; tough; semi-free. No tendency to crack.
- *Down.*—Moderately abundant; medium length.
- *Color.*—Relatively deep red (6–K–12), shading to (4–J–12) to lightest shade (3–A–12), the deeper red coloring being on part most exposed to the sun, with red mottling and streaking (5–J–11) on part unexposed to sun, and covered with grey bloom (44–B–1).

Flesh:
- *Amygdalin.*—Scant.
- *Juice.*—Moderate.
- *Texture.*—Firm; fine.
- *Fibers.*—Few.
- *Ripens.*—Uniformly; even.
- *Flavor.*—Sweet; mild.
- *Aroma.*—Slight.
- *Eating quality.*—Good to best.

*Color.*—Yellow (9–K–7) shading to (9–J–5) to (3–H–9) at stone, with slight red tinge from skin to stone.

Stone:

*Type.*—Free.

*Size.*—Medium to small. Average length—1½" to 1". Average breadth—1¼" to ⅞". Average thickness—¾".

*Form.*—Obovoid.

*Base.*—Flat; compressed.

*Hilum.*—Narrow.

*Apex.*—Acuminate.

*Sides.*—Equal.

*Surface.*—Irregularly furrowed near base. Pitted from above base to above center.

*Ridges.*—Rounded; on either side; interrupted near base on ventral edge.

*Pits.*—Rounded with acute point.

*Ventral edge.*—Thick; with base ridges interrupted.

*Dorsal edge.*—Narrow, with deep groove toward base.

*Tendency to split.*—None.

*Color.*—Light brown (14–F–9).

Use: Market; shipping, local and long distance; canning.

Keeping quality: Very good.
Shipping quality; Very good.

The tree and its fruit herein described may vary in slight detail due to climatic and soil conditions under which the variety may be grown.

The following is claimed:

A new and distinct variety of peach tree, substantially as illustrated and described, which bears large, rather uniform, evenly ripening, yellow firm fleshed—the flesh being slightly streaked with red—fully freestone fruit having a deep, glossy red, tough skin; the fruit—in comparison to the Gold Dust peach—being larger, more uniform in size and having a deeper red color;—in comparison to the July Elberta peach—by ripening about thirty days earlier and having a deeper red color;—in comparison to the Merrill Gem—by having a free stone and a finer, more melting taste; and being additionally characterized by fruit has superlative shipping and carrying qualities, ripening uniformly and evenly, good to best eating quality because of its relatively non acid taste, few fibers, excellent flavor which is fine and melting and no split pits.

No references cited.